(12) United States Patent
Yamka et al.

(10) Patent No.: US 9,808,027 B2
(45) Date of Patent: Nov. 7, 2017

(54) METHODS FOR PROMOTING HEALTH OR WELLNESS IN ADULT ANIMALS

(75) Inventors: Ryan Michael Yamka, Topeka, KS (US); Kim Gene Freisen, Topeka, KS (US); William David Schoenherr, Hoyt, KS (US)

(73) Assignee: Colgate-Palmolive Company, New York, NY (US)

( * ) Notice: Subject to any disclaimer, the term of this patent is extended or adjusted under 35 U.S.C. 154(b) by 1996 days.

(21) Appl. No.: 11/915,003

(22) PCT Filed: May 19, 2006

(86) PCT No.: PCT/US2006/019355
§ 371 (c)(1),
(2), (4) Date: Jul. 8, 2008

(87) PCT Pub. No.: WO2006/127424
PCT Pub. Date: Nov. 30, 2006

(65) Prior Publication Data
US 2008/0317905 A1    Dec. 25, 2008

Related U.S. Application Data

(60) Provisional application No. 60/682,978, filed on May 20, 2005.

(51) Int. Cl.
| | | |
|---|---|---|
| A23K 1/16 | (2006.01) | |
| A23K 50/40 | (2016.01) | |
| A61K 47/18 | (2017.01) | |
| A23K 20/142 | (2016.01) | |
| A23L 33/175 | (2016.01) | |

(52) U.S. Cl.
CPC .......... *A23K 50/40* (2016.05); *A23K 20/142* (2016.05); *A23L 33/175* (2016.08); *A61K 47/183* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,723,441 A | | 3/1998 | Higley et al. |
| 5,968,569 A | * | 10/1999 | Cavadini et al. .............. 426/61 |
| 6,039,952 A | * | 3/2000 | Sunvold et al. ......... 424/195.18 |
| 6,203,825 B1 | * | 3/2001 | Hodgkins ........................ 426/2 |
| 6,221,836 B1 | | 4/2001 | Beale et al. |
| 6,447,989 B1 | | 9/2002 | Comper |
| 6,458,767 B1 | | 10/2002 | Murphy-Ullrich et al. |
| 6,492,325 B1 | | 12/2002 | Cosgrove |
| RE38,167 E | | 7/2003 | Brown et al. |
| 6,589,748 B2 | | 7/2003 | Comper |
| 6,599,876 B2 | | 7/2003 | Kojima |
| 6,669,975 B1 | * | 12/2003 | Abene et al. ................. 426/302 |
| 6,784,159 B2 | | 8/2004 | Holub et al. |
| 2002/0028762 A1 | | 3/2002 | Kojima |
| 2002/0061897 A1 | * | 5/2002 | Elliott et al. .................. 514/258 |
| 2003/0180393 A1 | | 9/2003 | Stern |
| 2004/0081743 A1 | * | 4/2004 | Laflamme et al. ........... 426/630 |
| 2005/0026225 A1 | | 2/2005 | Comper |
| 2005/0249781 A1 | * | 11/2005 | Hirabayashi et al. ........ 424/439 |

FOREIGN PATENT DOCUMENTS

| | | |
|---|---|---|
| CA | 1068535 | 12/1979 |
| CA | 1211982 | 9/1986 |
| WO | 2004113570 A2 | 12/2004 |

OTHER PUBLICATIONS

Friedman, Journal of Agricultural and Food Chemistry, 49, Mar. 2001.*
Yamka, Animal Feed Science and Technology, 109, 2003.*
Bierer, J Nutr, 134, 2004.*
Chagnac, JASN, 14, 2003.*
Aoyama, Biosci Biotechnol Biochem, 64, 12, 2000.*
Morris, J.G., et al, "Lysine Requirement of Kittens Given Purified Diets for Maximal Growth," Journal of Animal Physiology and Animal Nutrition, vol. 88, No. 3-4, Apr. 1, 2004, pp. 113-116.

* cited by examiner

*Primary Examiner* — Susan Tran
*Assistant Examiner* — William Craigo

(57) ABSTRACT

Methods for promoting health or wellness, regulating food intake, and increasing nitrogen retention in an adult animal by feeding the animal a food containing lysine in an amount of at least about 3% by weight of total protein. Also, kits containing lysine and a food suitable for consumption in separate packages and instructions for how to combine the lysine and food are provided.

40 Claims, No Drawings

METHODS FOR PROMOTING HEALTH OR WELLNESS IN ADULT ANIMALS

CROSS-REFERENCE TO RELATED APPLICATIONS

This application is a United States National Stage Application under 35 U.S.C. 371 of International Application PCT/US2006/019355, filed May 19, 2006, which claims priority to U.S. Provisional Patent Application No. 60/682,978, filed May 20, 2005. The disclosures of the above applications are incorporated herein by reference.

BACKGROUND OF THE INVENTION

Field of the Invention

This invention relates generally to methods for promoting health or wellness in adult animals and particularly methods for promoting health or wellness in adult animals by feeding the animals a food containing relatively high amounts of lysine.

Description of the Prior Art

When developing foods for adult animals, consideration is given to the dietary intake of crude protein, carbohydrates, fat, vitamins, and minerals necessary to maintain health and wellness in such animals. Dietary protein, in addition to maintaining nitrogen balance, provides specific essential amino acids that cannot be synthesized by the body in sufficient amounts to meet maintenance requirements. The amount of a particular type or source of protein required in the diet depends on the ability of that protein to meet the animal's metabolic requirements for essential amino acids.

The number of animals considered overweight or obese is increasing. It is estimated that about 20% of humans are considered obese and between 25% and 40% of companion animals in the US are considered overweight or obese. An animal is considered overweight if it weighs more than 10% above ideal body weight and obese if it weighs more than 15% above ideal body weight. A companion animal has an ideal body weight if the animal's ribs can be felt but not seen. Obesity in companion animals is implicated in increased risk of diabetes mellitus, arthritis, pancreatitis, hepatic lipidosis, orthopedic disorders, cardiovascular disease, respiratory ailments, hip dysplasia, liver disease, gastrointestinal disorders, and skin problems. Owners often indulge their pets with treats, foods high in calories and fat, and table scraps. This overindulgence has an adverse effect on the health and wellness of the animal and often results in overweight animals with shortened lives. Pets along with their owners spend more time on the couch than exercising, exacerbating the problem. Some breeds of dogs or cats have particular propensities for rapid weight gain in spite of a diligent owner's attempts to curb the pet's increasing weight.

Humans and companion animals have been barraged with dieting schemes and exercise regimens to aid in controlling the animal's body weight. Advances have been made in the development of reduced calorie foods, low-fat foods, increased non-soluble fiber foods, low carbohydrate/high protein foods and other foods marketed for weight control. Still, the statistics indicate that opportunities for improvement remain and further advances in the art that promote the health or wellness of an animal are needed.

High protein, low carbohydrate diets are popular diets that can help an obese or overweight animal lose weight. Excess dietary protein, however, can be unsafe, particularly for senior animals and animals with renal disorders. For example, one in three elderly cats will die prematurely of chronic renal insufficiency, making it one of the leading causes of death in cats. Chronic renal insufficiency particularly affects cats over the age of seven years and occurs when areas of the kidney gradually become damaged and die. Left untreated, the continuous decline in kidney function makes it impossible for the body to eliminate waste, regulate electrolytes and conserve water. This leads to dehydration and a build-up of wastes in the blood stream, thus poisoning the animal. Increased dietary protein increases urinary nitrogen losses and places additional strain on an already stressed kidney and potentially causes further damage.

There is, therefore, a need for foods that promote health or wellness of an animal, particularly for senior animals, geriatric animals, and animals with renal disorders. Such foods should also reduce nitrogen excretion so that the foods are safe for the animals.

SUMMARY OF THE INVENTION

It is, therefore, an object of the present invention to provide methods for promoting the health or wellness of an adult animal.

It is another object of the present invention to provide methods for regulating food intake by an adult animal.

It is a further object of the present invention to provide methods for increasing nitrogen retention by an adult animal.

It is a further object of the invention to provide articles of manufacture in the form of kits that contain combinations of foods, compounds, and devices useful for promoting the health or wellness of an adult animal.

These and other objects are achieved using novel methods for promoting the health or wellness of an adult animal by feeding the animal a food comprising lysine in an amount of at least about 3% by weight of total protein. Kits comprising combinations of foods, compounds, and devices useful for promoting the health or wellness of an adult animal are also provided.

Other and further objects, features, and advantages of the present invention will be readily apparent to those skilled in the art.

DETAILED DESCRIPTION OF THE INVENTION

Definitions

The term "adult animal" means an animal of any age after the completion of juvenile growth and development, including senior and geriatric animals. For example, for humans "adult" typically means an age of about 18 years through the remainder of life and for cats and dogs "adult" typically means an age of about 1 year through the remainder of their life.

The term "animal" means a human or other animal, including avian, bovine, canine, equine, feline, hicrine, murine, ovine, and porcine animals.

The term "food" means compositions suitable for consumptions by an animal, including, but not limited to, dry food compositions, wet food compositions, and liquid food compositions.

The term "geriatric animal" means an animal showing outward signs of aging. Typically, a human over 75 years old and a dog or cat over 11 years old.

The term "health of an animal" means the absence of disease or infinity in the animal.

The term "in conjunction" means that a food and renal drug or other compound of the present invention are administered to an animal (1) together in a food composition or (2) separately at the same or different frequency using the same or different administration routes at about the same time or periodically. "Periodically" means that the renal drug is administered on a dosage schedule acceptable for a specific drug and that the food is fed to an animal routinely as appropriate for the particular animal. "About the same time" generally means that the food and renal drug are administered at the same time or within about 72 hours of each other. "In conjunction" specifically includes administration schemes wherein renal drugs are administered for a prescribed period and the compositions are administered indefinitely.

The term "lysine to ME ratio" means the amount of lysine in a food relative to the ME content of the food. The ratio can be expressed in any suitable units, for example g/Mcal or g/MJ. Unless otherwise indicated, the lysine to ME ratios herein are expressed in g/Mcal.

The term "metabolizable energy" (ME) in a food means the energy available to an animal by consumption of the food after energy excreted in feces, urine, and combustible gases has been subtracted.

The term "nitrogen retention" means the difference between nitrogen consumed by an animal and nitrogen excreted by the animal.

The term "protein" means molecules consisting essentially of amino acids.

The term "renal drug" means any compound, composition, or drug useful for preventing or treating renal insufficiency or dysfunction.

The term "senior animal" means an animal of an age having an increased risk for age-related disease but may or may not have obvious physical or behavioral characteristics of aging. Typically, a senior human is about 60 to about 75 years old and older, depending on breed, a senior dog, depending on breed, is about 5 to about 11 years old and a senior cat is about 7 to about 11 years old.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual food compositions physically associated such that they are considered a unit for manufacture, distribution, sale, or use.

The term "total protein" in a food means the total crude protein (CP). CP is typically measured by determining the total amount of nitrogen in a food, for example in g/kg, then multiplying that number by a conversion factor. When the food's primary protein source is corn, eggs or meat, or a combination of several protein sources, an appropriate conversion factor is 6.25. Maintenance guidelines of AAFCO (American Association of Feed Control Officials) recommend a minimum of 18% total protein in dog foods and a minimum of 26% total protein in cat foods, on a dry matter basis. AAFCO (2005) Official Publication.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

The term "wellness of an animal" means the complete physical, mental, and social well being of the animal, not merely the absence of disease or infirmity.

The Invention

The present invention provides methods for promoting health or wellness in an adult animal. The methods comprise feeding the animal a food comprising lysine in an amount of at least about 3% by weight of total protein. The methods are useful for promoting health or wellness of adult animals of any age or classification, including senior animals, geriatric animals, obese animals, overweight animals, and animals determined to be susceptible to or suffering from renal insufficiency or dysfunction.

In another aspect, the present invention provides methods for regulating food intake by an adult animal. The methods comprise feeding the animal a food comprising lysine in an amount of at least about 3% by weight of total protein. The methods are particularly useful for controlling an animal's weight, particularly for overweight or obese animals and animals having a tendency toward obesity.

In a further aspect, the present invention provides methods for increasing nitrogen retention by an adult animal. The methods comprise feeding the animal a food comprising lysine in an amount of at least about 3% by weight of total protein. Because excess nitrogen excretion is generally burdensome to an animal's kidneys, especially senior animals, geriatric animals, and animals with renal insufficiency or dysfunction, it is desirable to increase nitrogen retention in such animals.

Lysine useful in the present invention is obtained form any source, e.g., foods, proteins, and supplemental lysine in the form of an amino acid or its derivatives. Of the 20 or so amino acids that occur in proteins, some can be synthesized in the body in amounts sufficient to meet the body's requirements while others cannot and must be provided in the diet. Those required in the diet are known as essential amino acids; humans need eight essential amino acids, cats need eleven essential amino acids, and dogs need ten essential amino acids. Lysine is an essential amino acid required in the diet for balanced nutrition. Lysine is important in diets for growing animals and is generally the limiting amino acid in growth and development. According to NRC (1985) op. cit., growing dogs need 0.49% lysine on a dry matter basis in their food. AAFCO (1999) op. cit. recommends 0.77% lysine on a dry matter basis in dog food for growing dogs. For growing cats, NRC (1985) suggests 0.8% lysine on a dry matter basis in cat food, while AAFCO recommends 1.2%. Once an animal has completed its growth, however, industry standards substantially lower the recommended levels of lysine in the diet. NRC (1985) recommends 0.24% lysine on a dry matter basis in dog food for adult dogs, less than half the value it recommends for growing dogs. AAFCO recommends 0.63% lysine for adult dogs and 0.83% lysine for adult cats. These are minimum levels recommended for maintenance. Lysine requirements have typically been examined less for their significance in adult animals than in growing animals, and have generally not been optimized to promote health or wellness.

Table 1 shows the ideal amino acid profiles, expressed as ratios relative to lysine, in a diet for cats and dogs, assuming the diet contains the minimum lysine requirement as a percent of total food (0.70% for dogs and 0.80% for cats).

These ratios were estimated from studies in puppies and kittens. Baker and Czarnecki-Maulden (1991) Comparative Nutrition of Cats and Dogs 11, 239-263.

TABLE 1

Ideal Amino Acid Ratios (Relative to Lysine) for Cats and Dogs

| Amino acid | Cat | Dog |
| --- | --- | --- |
| Lysine | 100 | 100 |
| Methionine + cysteine | 100 | 64 |
| Tryptophan | 19 | 22 |
| Threonine | 87 | 67 |
| Arginine | 112 | 71 |
| Isoleucine | 63 | 57 |
| Valine | 75 | 75 |
| Leucine | 150 | 100 |
| Histidine | 38 | 29 |
| Phenylalanine + tyrosine | 112 | 100 |

The amount of lysine in the food is determined by the skilled artisan based upon the type and nature of the food and the animal, e.g., the age, weight, general health, and diet of the animal. While any amount greater than about 3% is acceptable, typical lysine amounts range from about 3% to about 15%, or from about 3% to about 9%, or from about 3% to about 6%. In various embodiments, the amount of lysine is at least about 3.5%, at least about 4%, at least about 4.5%, or at least about 5% by weight of total protein.

Generally, the lysine to ME ratio of a food useful according to the present invention is at least about 1.5:1. In one embodiment, the lysine to ME ratio of a dog food useful according to the invention is at least about 1.7:1. In other embodiments, the lysine to ME ratio of a dog food is at least about 2:1, about 1.7:1 to about 5:1, or about 2:1 to about 5:1. In another embodiment, the lysine to ME ratio of a cat food useful according to the invention is at least about 3.2:1. In other embodiments, the lysine to ME ratio of a cat food is at least about 5:1, about 3.2:1 to about 10:1, or about 5:1 to about 10:1. Skilled artisans can calculate the desired ratio for various animals.

The foods useful in the present invention can be any common food edible by an animal. Common protein sources used in formulating foods include meats and fish, dairy and egg products, vegetables, and baker's yeast. Such dietary protein sources, when used in foods, provide amino acids required for energy and synthesis of tissues, enzymes, albumins, hormones, and other nitrogen containing compounds.

Foods of the present invention include canned moist foods and extruded dry foods having lysine as an ingredient in amounts as set forth herein. Any animal can benefit from inclusion of lysine at such levels in foods. In one embodiment, the food is one having a major (at least about 25%, for example at least about 50%, by weight) component derived from animal (e.g., mammal, bird, fish or seafood) proteinaceous tissues including muscle tissues and/or offal, optionally with a carbohydrate source such as cereal grains.

Substantially all protein sources contain lysine. This naturally present lysine contributes a baseline amount of lysine when a typical protein source is formulated into a food. Supplemental lysine herein is any lysine added to a food above the baseline amount. Supplemental lysine can be added as lysine per se, or more typically in the form of lysine-rich proteins such as casein, whey, fish meal, chicken and poultry by-products, dried whole egg, or soybean meal. The supplemental lysine can be distributed more or less homogeneously through the food or can be present on surfaces of food pieces such as meat chunks or dry kibbles.

Where supplemental lysine is localized on surfaces of food pieces, local concentrations can exceed those of the present invention provided that the overall amount in the food as a whole is in the amounts set fourth herein in percentage of total protein or in lysine to ME ratio.

In preparing a food useful according to the present invention, the components of the food are adjusted so that the baseline lysine and supplemental lysine together (or total lysine) are present in the food at a desired percentage of total protein and lysine to ME ratio. The supplemental lysine can, for example, be incorporated into the food during formulation, such as during and/or after mixing of other components of the composition. Distribution of these components into the composition can be accomplished by any conventional method including standard mixing procedures.

Foods useful in the method of the invention can be prepared in a wet or containerized (e.g., canned or in pouches) form using conventional pet food processes. In one contemplated embodiment, ground animal (e.g., mammal, poultry, fish and/or seafood) proteinaceous tissues are mixed with other ingredients, including for example, animal fats and vegetable oils, cereal grains, other nutritionally balancing ingredients, and special purpose additives (e.g., vitamin and mineral mixtures, inorganic salts, cellulose and beet pulp, bulking agents, and the like). Water sufficient for processing is also added. These ingredients typically are mixed in a vessel suitable for heating while blending the components. Heating of the mixture can be effected in any suitable manner, such as, for example, by direct steam injection or by using a vessel fitted with a heat exchanger. Following addition of the last of these ingredients, the mixture is heated in a pre-cooking step to a temperature of up to about 100° C. Higher temperatures can be acceptable, but can be commercially impractical without use of other processing aids. When heated to the appropriate temperature, the material is typically in the form of a thick liquid. The thick liquid is filled into suitable containers such as cans, jars, pouches or the like. A lid is applied, and the container is hermetically sealed. The sealed containers are then placed into conventional equipment designed to sterilize the contents. This is usually accomplished by heating to a temperature of at least about 110° C. for an appropriate time, which is dependent on, for example, the temperature used and the composition. Products can also be prepared by an aseptic process wherein the contents are heated to commercial sterility before being packaged in sterilized containers. Supplemental lysine can be added to containerized food products before, during or after the pre-cooking step.

Foods useful in the method of the invention can be prepared in a dry form using conventional processes. In one contemplated embodiment, dry ingredients, including, for example, animal protein sources, plant protein sources, grains, etc., are ground and mixed together. Moist or liquid ingredients, including fats, oils, animal protein sources, minerals, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which can include, for example, flavors, fats, oils, powders, and the like. Kibble also can be made from the dough using a baking process, rather than extrusion, wherein the dough is placed into a mold before dry-heat processing. Kibble also can be made from a food matrix undergoing pelletization.

The supplemental lysine can be incorporated into the food by addition to the above-described mixtures before extrusion or by coating extruded kibble or pellets with supplemental lysine as an ingredient of a topical coating. For example, supplemental lysine can be added to liquids in a dry processing line, to a pre-conditioner composition or to a coating composition. Supplemental lysine can, if desired, be encapsulated in food systems. For example, supplemental lysine can be added to a palatant (such as a digest or broth) at any time during processing of the palatant.

The method of the present invention is useful to promote health or wellness for a variety of animals, including human and non-human animals such as non-human primates (e.g., monkeys, chimpanzees, etc.), companion animals (e.g., dogs, cats, horses, etc.), food animals (e.g., goats, chickens, sheep, swine, cattle, etc.), laboratory animals (e.g., mice, rats, etc.), birds (e.g., domestic birds such as canaries, parrots, etc. and commercial birds such as chickens, ducks, turkeys, etc.), rodents (e.g., hamsters, guinea pigs, gerbils, rabbits, hedgehogs, ferrets, chinchillas, etc.) and wild, exotic and zoo animals (e.g., wolves, bears, deer, etc.).

In a further aspect, the present invention provides methods for promoting health or wellness in an adult animal. The methods comprise feeding in conjunction a health or wellness promoting amount of a renal drug and a food comprising lysine in an amount of at least about 3% by weight of total protein. Renal drags useful in the invention are any renal drugs known to skilled artisans to be useful for combating renal insufficiency or dysfunction. Preferred drugs include lysosome-activating compounds such as those described in U.S. Pat. No. 6,589,748, triterpene saponins such as those described in U.S. Pat. No. 6,784,159, activin inhibitors such as those described in U.S. Pat. No. 6,599,876 and US Patent Application Number (USPAN) 20020028762, integrin receptor inhibitors and TGF inhibitors such as those described in U.S. Pat. No. 6,492,325, TGF activation inhibitors such as those described in U.S. Pat. No. 6,458,767, and insulin-like growth factor (IGF) as described in U.S. Pat. No. 5,723,441. Most Preferred drugs include Converting Enzyme (ACE) inhibitors, androgens, erythropoiten, and calcitriol. Angiotensin and endothelin are potent systemic vasoconstrictors with specific intrarenal effects that contribute to progressive renal injury. A variety of renal drugs are used to mitigate the effect of these vasoconstrictors. Angiotensin converting enzyme inhibitors (enalapril—Enacard and Vasotec and benazepril—Lotensin) have been associated with a reduction in the severity of proteinuria and slowing of progression of renal failure. The ACE inhibitor enalapril (Enacard, Vasotec) limits glomerular and systemic hypertension, proteinuria, and glomerular and tubulointerstitial lesions. Angiotensin blockers and endothelin inhibitors have beneficial effects in renal disease. Vasopeptide inhibitors are agents that inhibit both ACE and neutral endopeptidase, an enzyme involved in the breakdown of natriuretic peptides, adrenomedullin, and bradykinin. These renal drugs decrease angiotenin II production and increase accumulation of vasodilators. Renal patients with systemic hypertension respond to calcium channel blockers such as amlodipine (Norvasc). Uremic gastritis (esophagitis, gastritis, gastric ulceration and hemorrhage) is treated with H2 receptor antagonists (cimetidine—Tagamet, famotidine—Pepcid), proton pump blockers (omeprazole—Prilosec), cytoprotective agents (misoprostol—Cytotec), and antiemetic drugs that effect the emetic center (chlorpromazine—Thorazine, perchlorperazine—Compazine, metoclopramide—Reglan). Androgens or anabolic steroids (Stanozol, Winstrol—V) are used in the treatment of anemia associated with chronic renal failure. Hormone replacement therapy using recombinant human (or other species) erythropoiten (Epoetin alpha, Epogen, Procrit) is the treatment of choice for severe anemia associated with renal failure. Phosphate binders (aluminum hydroxide—Amphojel, aluminum carbonate—Basaljel) are used to control hyperphosphatemia and secondary renal hyperparathyroidism. Calcitriol (1, 25-dihydroxycholecalciferol) (Rocaltrol) and vitamin D analogues cause a calcium-independent suppression of parathyroid hormone (PTH). Administration of phosphate binders, calcitriol and related compounds has been advocated in chronic renal failure to prevent multi-system toxicity caused by PTH. Potassium depletion and hypokalemia are common in cats with chronic renal failure. Oral supplementation of potassium in the form of potassium gluconate (Tumil K, RenaKare, Kolyum) or citrate is recommended. Holistic renal drugs and compositions are also included in the present invention. Preferred holistic renal drugs include cranberry extract and mannose. Cranberry extract is purported to reduce the prevalence of urinary tract infection which is a common risk factor for long-term decline of renal function. Renal drugs include typical small molecule pharmaceuticals, small proteins, macromolecular proteins and molecules, and antibodies and further include vaccines designed to prevent renal disease. Antibodies include polyclonal and monoclonal antibodies and immunoglobulin fragments such as Fv, Fab, Fab', F(ab')2, or other antigen-binding antibody subsequences that interact with an antigen and perform the same biological function as a native antibody. The renal drugs are administered to the patient using any method appropriate for the renal drug and in amounts known to skilled artisans to be sufficient to treat or prevent renal disease.

In another aspect, the present invention also provides methods for promoting health or wellness in an adult animal. The methods comprise feeding in conjunction a health or wellness promoting amount of a gastrointestinal tract improving agent selected from the group consisting of probiotics and prebiotics and a food comprising lysine in an amount of at least about 3% by weight of total protein. Probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Prebiotics are nondigestible food ingredients that beneficially affect host health by selectively stimulating the growth and/or activity of bacteria in the colon. The prebiotic, fructooligosaccharide (FOS) is found naturally in many foods such as wheat, onions, bananas, honey, garlic, and leeks. FOS can also be isolated from chicory root or synthesized enzymatically from sucrose. FOS fermentation in the colon results in a large number of physiologic effects including increasing the numbers of bifidobacteria in the colon, increasing calcium absorption, increasing fecal weight, shortening of gastrointestinal transit time, and possibly lowering blood lipid levels. The increase in bifidobacteria has been assumed to benefit human health by producing compounds to inhibit potential pathogens, by reducing blood ammonia levels, and by producing vitamins and digestive enzymes. Probiotic bacteria such as Lactobacilli or Bifidobacteria are believed to positively affect the immune response by improving the intestinal microbial balance leading to enhanced antibody production and phagocytic (devouring or killing) activity of white blood cells. Bifidobacterium lactis could be an effective probiotic dietary supplement for enhancing some aspects of cellular immunity in the elderly. Probiotics enhance systemic cellular immune responses and may be useful as a dietary supplement to boost natural immunity in otherwise healthy adults. Probiotics include many types of bacteria but generally are selected from four genera of bacteria: Lactobacilllus acidophillus, Bifidobacteria, Lactococcus, and Pediococcus. The amount of probiotics and prebiotics to be administered to the animal is determined by the skilled artisan based upon the type and nature of the prebiotic and probiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, preferably from about 5 billion to about 10 billion live bacteria per day. Generally, prebiotics are administered in amounts sufficient to positively stimulate the healthy microflora in the gut and cause these "good" bacteria to reproduce. Typical amounts are from about one to about 10 grams per serving or from about 5 percent to about 40 percent of the recommended daily dietary fiber for an animal. The probiotics and prebiotics can be made part of the composition by any suitable means. Generally, the agents are mixed with the composition or applied to the surface of the composition, e.g., by sprinkling. When the agents are part of a kit, the agents can be admixed with other materials or in their own package.

In another aspect, the present invention provides a means for communicating information about or instructions for promoting health or wellness in an adult animal, regulating food intake by an adult animal, increasing nitrogen retention by an adult animal, feeding in conjunction a health or wellness promoting amount of a renal drug and a food comprising lysine in an amount of at least about 3% by weight of total protein, and using renal diagnostic devices for determining kidney function and evaluating the presence and severity of renal insufficiency or dysfunction. The communicating means comprises a document, digital storage media, optical storage media, audio presentation, or visual display containing the information or instructions. Preferably, the communication is a displayed web site or a brochure, product label, package insert, advertisement, or visual display containing such information or instructions. Useful information includes one or more of (1) methods and techniques for combining and feeding the lysine, foods, and renal drags, (2) information for using the renal diagnostic devices, (3) details about the side effects, if any, caused by using the present invention in combination with other drugs, and (4) contact information for patients to use if they have a question about the invention and its use. Useful instructions include dosages, administration amounts and frequency, and administration routes. The communication means is useful for instructing on the benefits of using the present invention and communicating the approved methods for making or feeding the invention to an animal.

In a further aspect, the present invention provides a kit comprising in separate containers in a single package lysine and a food, wherein the lysine and the food are present in amounts sufficient to produce a food comprising lysine in an amount of at least about 3% by weight of total protein when combined. In other embodiments, the kits further comprise one or more renal drugs. Typically, the renal drugs are in a separate package or in the package with one of the other kit components. In other embodiments, the kits further comprise one or more renal diagnostic devices for determining kidney function and evaluating the presence and severity of renal insufficiency or dysfunction in an animal. The renal diagnostic devices are typically in a separate package but may be in the package with one of the other kit components. The renal diagnostic devices useful in the present invention include any device suitable for determining kidney function and evaluating the presence and severity of renal insufficiency or dysfunction in an animal. Preferred diagnostic methods include serum urea nitrogen (SUN), creatinine levels, urine specific gravity, and DNA damage, including urine assays for albumin such as those described in U.S. Pat. Nos. 6,589,748, 6,447,989 and USPAN 20050026225 and comet trail assays. Diagnostic methods are based upon known techniques including (1) blood markers such as elevated blood urea nitrogen concentration, elevated serum creatinine concentration, hyperphosphatemia, hyperkalemia or hypokalemia, metabolic acidosis and hypoalburinemia, (2) urine markers such as impaired urine concentrating ability, proteinuria, cylinduria, renal hematuria, inappropriate urine pH, inappropriate urine glucose concentration, and cystinuria, (3) physical, imaging, and diagnostic markers such as size, shape, location, and density, (4) single nucleotide polymorphisms (SNPs) such as those disclosed in WO 2004113570 A2, (5) genetic profiles that are indicative of renal insufficiency or dysfunction, (6) proteomic profiles that are indicative of renal insufficiency or dysfunction, and (7) metabolic profiles that are indicative of renal insufficiency or dysfunction. These diagnostic methods and devices (e.g., test strips, ELISA assays, comet assays,) based upon such methods are commonly available to skilled artisans such as scientists and health care professionals and many are available to consumers, e.g., the Heska Corporation's (Fort Collins Colo.) E.R.D.-HealthScreen Urine Tests that detects small amounts of albumin in the urine ("microalbuminuria"). In additional embodiments, the kits further comprise at least one of a means for communicating information about or instructions for promoting health or wellness in an adult animal, regulating food intake by an adult animal, increasing nitrogen retention by an adult animal, feeding in conjunction a health or wellness promoting amount of a renal drug and a food comprising lysine in an amount of at least about 3% by weight of total protein, and using renal diagnostic devices for determining kidney function and evaluating the presence and severity of renal insufficiency or dysfunction. In other embodiments, the kits further comprise one or more gastrointestinal tract improving agents selected from the group consisting of probiotics and prebiotics.

In an additional aspect, the present invention provides a kit comprising in separate containers in a single package or in separate containers in a virtual package, as appropriate, a food comprising lysine in an amount of at least about 3% by weight of total protein and at least one of (1) a renal drug, (2) a renal device, (3) one or more of a means for communicating information about or instructions for promoting health or wellness in an adult animal, regulating food intake by an adult animal, increasing nitrogen retention by an adult animal, feeding in conjunction a health or wellness promoting amount of a renal drug and a food comprising lysine in an amount of at least about 3% by weight of total protein, and using renal diagnostic devices for determining kidney function and evaluating the presence and severity of renal insufficiency or dysfunction, and (4) a gastrointestinal tract improving agent selected from the group consisting of probiotics and prebiotics.

The kit components are typically in a separate package, in or on the package with one of the other kit components, or in a virtual package, as appropriate for the type of kit component. When the kit comprises a virtual package, the kit is limited to the instructions in a virtual environment in combination with one or more of the other physical kit components.

The present invention further provides a process for manufacturing a food comprising lysine in an amount of at least about 3% by weight of total protein. The process comprises adding supplemental lysine to a food in amounts sufficient to produce a food having at least about 3% by weight of total protein. The process can be accomplished using methods known to skilled artisans, e.g., by admixing the lysine into the food, by applying the lysine onto the food as a powder, or a spraying solution of lysine onto the food. The present invention also provides the product produced by the process. The present invention also provides a food comprising lysine in an amount of at least about 3% by weight of total protein. The lysine to ME ratio of the food is at least about 1.5:1.

The methods, kits, processes, and compositions are useful for (1) promoting health or wellness in an adult animal, (2) regulating food intake by an adult animal, or (3) increasing nitrogen retention by an adult animal. The methods, kits, processes, and compositions have specific benefits for senior animals, geriatric animals, obese animals, animals that tend toward obesity, and animals determined to be susceptible to or suffering from renal insufficiency or dysfunction.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

Forty-two (42) cats were divided into seven groups and each group was placed on one of seven diets. The composition of each diet is shown in Table 2. A formulated nutrient value derived from historical data is calculated by adding the amounts of nutrient provided by each individual ingredient of the composition. An observed nutrient value is the amount of a nutrient in a composition as determined by analysis of the final composition. The cats were fed the assigned diet daily for twenty-one (21) days and intake measurements were made 24 hours after each feeding. The results are shown in Table 2. The two diets with the highest formulated and observed lysine to ME ratios. Foods 6 and 7 showed the lowest average daily intakes per kg of body weight.

TABLE 2

Nutrient Values and Intake Amounts of Cat Foods

| Item | Food 1 | Food 2 | Food 3 | Food 4 | Food 5 | Food 6 | Food 7 |
|---|---|---|---|---|---|---|---|
| Formulated values | | | | | | | |
| ME, kcal/kg | 4463 | 4366 | 4366 | 4673 | 4205 | 4221 | 4214 |
| Lysine, % DM | 1.5 | 1.5 | 1.5 | 2.0 | 2.0 | 3.2 | 3.3 |
| CP, % DM | 33 | 31.5 | 29.5 | 54.5 | 54.5 | 55 | 51.7 |
| Lysine, % CP | 4.5 | 4.8 | 5.1 | 3.7 | 3.7 | 5.8 | 6.4 |
| Lysine:ME, g/Mcal | 3.3 | 3.4 | 3.4 | 4.2 | 4.7 | 7.7 | 7.8 |
| CP:ME, g/Mcal | 73.9 | 72.1 | 67.6 | 116.6 | 129.6 | 130.3 | 122.7 |
| Intake, g/day/kg BW | 15 | 16 | 21 | 16.0 | 19.3 | 13.1 | 14.5 |
| Observed values | | | | | | | |
| Lysine:ME, g/Mcal | 3.07 | 3.16 | 3.11 | 3.76 | 4.13 | 6.92 | 7.17 |
| CP:ME, g/Mcal | 66.14 | 64.85 | 61.10 | 101.28 | 103.81 | 112.09 | 105.57 |
| ME, kcal/kg | 4761 | 4742 | 4825 | 5250 | 4784 | 4682 | 4605 |
| Feed Analysis (On 100% DM basis) | | | | | | | |
| Moisture, % of total | 6.95 | 7.32 | 7.4 | 5.21 | 5.76 | 5.49 | 4.97 |
| Fat, % DM | 23.6 | 21.4 | 21.5 | 27.3 | 23.0 | 24.1 | 23.3 |
| Ash, % DM | 5.1 | 5.2 | 5.2 | 6.2 | 8.5 | 6.6 | 5.4 |
| Crude Fiber, % DM | 2.4 | 2.7 | 2.3 | 1.5 | 5.0 | 7.1 | 5.8 |
| CP, % DM | 31.5 | 30.8 | 29.5 | 53.2 | 49.7 | 52.5 | 48.6 |

Key:
CP = crude protein,
ME = metabolizable energy,
BW = body weight,
DM = dry matter

Example 2

Eight (8) dogs were divided into five groups and each group was placed on one of five diets. The composition of each diet is shown below in Table 3. Dogs were fed the assigned diet daily for 14 days. The results are shown in Table 3. Food 5 had the greatest lysine to ME ratio (based on either formulated or observed ME) and also resulted in greater nitrogen retention.

TABLE 3

Nutrient Values and Nitrogen Retention for Dog Food Diets

| Item | Food 1 | Food 2 | Food 3 | Food 4 | Food 5 |
|---|---|---|---|---|---|
| DM, % of total | 96.3 | 95.9 | 95.8 | 94.3 | 97.1 |
| CP, % DM | 19.4 | 21.4 | 21.7 | 18.4 | 19.6 |
| Crude Fat, % DM | 9.4 | 10.1 | 4.9 | 3.7 | 7.0 |
| Crude Fiber, % DM | 2.8 | 2.8 | 3.0 | 3.1 | 3.2 |
| Ash, % DM | 4.0 | 4.5 | 5.5 | 4.5 | 5.5 |
| Lysine, % DM | 0.88 | 0.95 | 1.0 | 0.91 | 1.03 |
| Lysine, % CP | 4.5 | 4.4 | 4.6 | 4.9 | 5.3 |
| ME kcal/kg DM (Formulated) | 3800 | 3800 | 3800 | 3800 | 3780 |
| ME kcal/kg DM (Observed) | 3890 | 3737 | 3614 | 3463 | 3985 |
| Nitrogen Retention (Observed) g/d | 1.3 | 1.2 | 0.7 | 1.0 | 1.6 |
| Digestible Lysine:ME (Formulated) g/Mcal | 1.78 | 1.89 | 1.72 | 1.66 | 2.16 |
| Digestible Lysine:ME (Observed) g/Mcal | 1.73 | 1.91 | 1.80 | 1.83 | 2.05 |
| Digestible Protein:ME (Formulated) g/Mcal | 40.3 | 46.2 | 38.3 | 33.9 | 37.3 |
| Digestible Protein:ME (Observed) g/Mcal | 39.4 | 47.0 | 40.2 | 37.2 | 35.4 |

Key:
CP = crude protein,
ME = metabolizable energy,
DM = dry matter

Referring to Tables 2 and 3, the results show that feeding an animal a diet relatively high in lysine promotes the health or wellness of the animal.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a palatant" includes a plurality of such palatants or reference to pieces includes a single piece. The words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compounds and methodologies reported therein that might be used with the present invention. However, nothing herein is to be construed as an admission that the invention is not entitled to antedate such disclosure by virtue of prior invention.

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A method for promoting health or wellness in a senior or geriatric canine adult animal, comprising:
   feeding the canine adult animal a canned moist food;
   wherein the canine adult animal is overweight or obese,
   wherein the promoting of the health or wellness comprises controlling a body weight of the canine adult animal,
   wherein the canned moist food comprises:
      a protein source providing baseline lysine in an amount less than 3% by weight of total protein in the canned moist food;
      a source of supplemental lysine in an amount sufficient to raise an overall amount of lysine in the canned moist food to at least 4% by weight of the total protein; and
      one or more probiotics; and
   wherein a ratio of the overall amount of lysine to metabolizable energy is about 5 grams per megacalorie (Mcal).

2. The method of claim 1, wherein the source of the supplemental lysine is in an amount sufficient to raise the overall amount of lysine in the canned moist food to at least 5% by weight of the total protein.

3. The method of claim 1, wherein the source of the supplemental lysine is in an amount sufficient to raise the overall amount of lysine in the canned moist food to about 6% by weight of the total protein.

4. The method of claim 1, wherein the source of the supplemental lysine is in an amount sufficient to raise the overall amount of lysine in the canned moist food to about 9% by weight of the total protein.

5. The method of claim 1, wherein the source of the supplemental lysine is in an amount sufficient to raise the overall amount of lysine in the canned moist food to about 15% by weight of the total protein.

6. The method of claim 1, wherein the source of the supplemental lysine comprises lysine per se.

7. The method of claim 1, wherein the source of the supplemental lysine comprises casein.

8. The method of claim 1, wherein the source of the supplemental lysine comprises whey.

9. The method of claim 1, wherein the source of the supplemental lysine comprises fish meal, chicken and poultry by-products, dried whole egg, or soybean meal.

10. The method of claim 1, wherein the canned moist food further comprises one or more probiotics.

11. A method for promoting health or wellness in a senior or geriatric feline adult animal, comprising:
   feeding the feline adult animal a canned moist food;
   wherein the feline adult animal is overweight or obese,
   wherein the promoting of the health or wellness comprises controlling a body weight of the feline adult animal,
   wherein the canned moist food comprises:
      a protein source providing baseline lysine in an amount less than 3% by weight of total protein in the canned moist food;
      a source of supplemental lysine in an amount sufficient to raise an overall amount of lysine in the canned moist food to at least 4% by weight of the total protein; and
      one or more probiotics; and wherein a ratio of the overall amount of lysine to metabolizable energy is about 10 grams per megacalorie (Mcal).

12. The method of claim 11, wherein the source of the supplemental lysine is in an amount sufficient to raise the overall amount of lysine in the canned moist food to at least 5% by weight of the total protein.

13. The method of claim 11, wherein the source of the supplemental lysine is in an amount sufficient to raise the overall amount of lysine in the canned moist food to about 6% by weight of the total protein.

14. The method of claim 11, wherein the source of the supplemental lysine is in an amount sufficient to raise the overall amount of lysine in the canned moist food to about 9% by weight of the total protein.

15. The method of claim 11, wherein the source of the supplemental lysine is in an amount sufficient to raise the overall amount of lysine in the canned moist food to about 15% by weight of the total protein.

16. The method of claim 11, wherein the source of the supplemental lysine comprises lysine per se.

17. The method of claim 11, wherein the source of the supplemental lysine comprises casein.

18. The method of claim 11, wherein the source of the supplemental lysine comprises whey.

19. The method of claim 11, wherein the source of the supplemental lysine comprises fish meal, chicken and poultry by-products, dried whole egg, or soybean meal.

20. The method of claim 11, wherein the canned moist food further comprises one or more probiotics.

21. A method for promoting health or wellness in a senior or geriatric canine adult animal, comprising:
   feeding the canine adult animal a canned moist or dry food;
   wherein the canine adult animal is overweight or obese,
   wherein the promoting of the health or wellness comprises controlling a body weight of the canine adult animal,
   wherein the canned moist food comprises:
      a protein source providing baseline lysine in an amount less than 3% by weight of total protein in the canned moist food;
      a source of supplemental lysine in an amount sufficient to raise an overall amount of lysine in the canned moist food to at least 4% by weight of the total protein;
      arginine, histidine, isoleucine, leucine, methionine, phenylalanine, threonine, tryptophan, and valine; and
      one or more probiotics; and
   wherein a ratio of the overall amount of lysine to metabolizable energy is about 5 grams per megacalorie (Mcal).

22. The method of 21, wherein the source of the supplemental lysine is in an amount sufficient to raise the overall amount of lysine in the canned moist food to at least 5% by weight of the total protein.

23. The method of claim 21, wherein the source of the supplemental lysine is in an amount sufficient to raise the overall amount of lysine in the canned moist food to about 6% by weight of the total protein.

24. The method of claim 21, wherein the source of the supplemental lysine is in an amount sufficient to raise the overall amount of lysine in the canned moist food to about 9% by weight of the total protein.

25. The method of claim 21, wherein the source of the supplemental lysine is in an amount sufficient to raise the overall amount of lysine in the canned moist food to about 15% by weight of the total protein.

26. The method claim 21, wherein the source of the supplemental lysine comprises lysine per se.

27. The method of claim 21, wherein the source of the supplemental lysine comprises casein.

28. The method of claim 21, wherein the source of the supplemental lysine comprises whey.

29. The method of claim 21, wherein the source of the supplemental lysine comprises fish meal, chicken and poultry by-products, dried whole eggs, or soybean meal.

30. The method of claim 21, wherein the canned moist food further comprises one or more prebiotics.

31. A method for promoting health or wellness in a senior or geriatric feline adult animal, comprising;
   feeding the feline adult animal a canned moist or dry food;
   wherein the feline adult animal is overweight or obese,
   wherein the promoting of the health or wellness comprises controlling a body weight of the feline adult animal,
   wherein the canned moist food comprises:
      a protein source providing baseline lysine in an amount less than 3% by weight of total protein in the canned moist food;
      a source of supplemental lysine in an amount sufficient to raise an overall amount of lysine in the canned moist food to at least 4% by weight of the total protein;
      arginine, histidine, isoleucine, leucine, methionine, phenylalanine, threonine, tryptophan, and valine; and
      one or more probiotics; and
   wherein a ratio of the overall amount of lysine to metabolizable energy is about 10 grams per megacalorie (Mcal).

32. The method of claim 31, wherein the source of the supplemental lysine is in an amount sufficient to raise the overall amount of lysine in the canned moist food to at least 5% by weight of the total protein.

33. The method of claim 31, wherein the source of the supplemental lysine is in an amount sufficient to raise the overall amount of lysine in the canned moist food to about 6% by weight of the total protein.

34. The method of claim 31, wherein the source of the supplemental lysine is in an amount sufficient to raise the overall amount of lysine in the canned moist food to about 9% by weight of the total protein.

35. The method of claim 31, wherein the source of the supplemental lysine is in an amount sufficient to raise the overall amount of lysine in the canned moist food to about 15% by weight of the total protein.

36. The method of claim 31, wherein the source of the supplemental lysine comprises lysine per se.

37. The method of claim 31, wherein the source of the supplemental lysine comprises casein.

38. The method of claim 31, wherein the source of the supplemental lysine comprises whey.

39. The method of claim 31. wherein the source of the supplemental lysine comprises fish meal, chicken and poultry by-products, dried whole egg, or soybean meal.

40. The method of claim 31, wherein the canned moist food further comprises one or more prebiotics.

* * * * *